United States Patent [19]

Melas

[11] Patent Number: 4,741,894
[45] Date of Patent: May 3, 1988

[54] METHOD OF PRODUCING HALIDE-FREE METAL AND HYDROXIDES

[75] Inventor: Andreas A. Melas, Burlington, Mass.
[73] Assignee: Morton Thiokol, Inc., Chicago, Ill.
[21] Appl. No.: 870,070
[22] Filed: Jun. 3, 1986
[51] Int. Cl.$^4$ .................. C01B 13/14; C22B 34/24
[52] U.S. Cl. .................. 423/592; 423/63; 423/66; 423/69; 423/608; 423/609; 423/611
[58] Field of Search ............ 423/63, 66, 67, 592, 423/608, 609, 610, 611

[56] References Cited

U.S. PATENT DOCUMENTS

| | | | |
|---|---|---|---|
| 4,507,245 | 3/1985 | Ozaki et al. | 534/15 |
| 4,543,341 | 9/1985 | Barringer et al. | 423/608 |
| 4,673,554 | 6/1987 | Niwa et al. | 423/63 |

FOREIGN PATENT DOCUMENTS

| | | | |
|---|---|---|---|
| 3428788 | 8/1984 | Fed. Rep. of Germany | 423/592 |
| 6065759 | 9/1983 | Japan | 423/66 |

OTHER PUBLICATIONS

Kirk Othmer, Encyclopedia of Chemical Technology, Third Ed., vol. 2, Alkoxides, Metal to Antibiotics Peptides, p. 218, 1973.

D. C. Bradley, R. C. Mehrotra & D. P. Gaur, *Metal Alkoxides,* Academic Press, London (1978) pp. 13–15,1–50–151,165–166, 345,360.

*Primary Examiner*—Patrick P. Garvin, Sr.
*Assistant Examiner*—Paige C. Harvey
*Attorney, Agent, or Firm*—Gerald K. White; Wayne E. Nacker

[57] ABSTRACT

Niobium (V) and tantalum (V) halides are converted to $Nb_2O_5$ and $Ta_2O_5$ that are free of detectable levels of halide in a two step process. In the first step, the metal halide is reacted with an alcohol and with a replacement species, such as ammonia, which reacts with the halide. This produces a metal alkoxide which is soluble and a halide salt of the replacement species which is insoluble in the alcohol and precipitates. After physically separating the alkoxide in alcohol solution from the precipitate, in a second step, the metal alkoxide is hydrolyzed with purified water to produce the oxide.

12 Claims, No Drawings

METHOD OF PRODUCING HALIDE-FREE METAL AND HYDROXIDES

The present invention is directed to producing highly purified metal oxides or hydroxides, particularly metal oxides and metal hydroxides which are free of chlorides.

BACKGROUND OF THE INVENTION

There exists a need for highly pure metal oxides and hydroxides, and particularly for highly pure oxides and hydroxides of transition metals, including the rare earth metals. One application for highly purified oxides and hydroxides is the growth of crystals having particular optical characteristics; for example, it has been found that crystals of very pure $LiTaO_3$ and $LiNbO_3$ are useful in laser systems to double the frequency of $CO_2$ lasers. To grow $LiTaO_3$ or $LiNbO_3$ crystals, highly purified tantalum (V) oxide ($Ta_2O_5$) and niobium (V) oxide ($Nb_2O_5$) are required. Highly purified transition metal oxides are also useful in the electronic industry.

In cases where the metal is directly convertible to the oxide by burning, particularly in the case of the alkali metals and the alkaline earth metals, substantially pure metal oxides are obtainable by direct oxidation of the metals. In the case of many transition metals, including rare earth metals, direct oxidation is impractical, and the oxides are typically produced by hydrolysis of the corresponding halide. For example, tantalum (V) oxide and niobium (V) oxide are generally produced by hydrolysis of the corresponding chlorides:

$$2TaCl_5 + 5H_2O \rightarrow Ta_2O_5 + 10HCl$$

$$2NbCl_5 + 5H_2O \rightarrow Nb_2O_5 + 10HCl.$$

It has been found, however, that metal oxides, and metal hydroxides such as those currently produced by hydrolysis of chlorides, lack sufficient purity for many highly technical applications, such as growing optical grade crystals. In particular, commercial grade oxides of many metals contain a substantial amount of the halide as mixed oxide/halides. Apparently, the bond between the metals and the halide is sufficiently strong that complete removal of the halide by aqueous hydrolysis is not achieved. Furthermore, there do not exist practical means for completely separating the mixed oxide/halides from the metal oxides.

SUMMARY OF THE INVENTION

In accordance with the invention, oxides and hydroxides which are free of detectable levels of halides, particularly transition metal oxides, are produced from corresponding halides. In a first step of a two-step procedure, an alcohol-reactive starting compound, which is a halide of the subject element of which a pure oxide is desired, is reacted with a water-free alcohol to form the corresponding alkoxide. The alcohol is selected such that the subject element alkoxide is soluble but halide salts are insoluble. Suspended particles of the starting compound are exposed to the alcohol and also to an alkali metal, an alkaline earth metal or ammonia, resulting in complete conversion of the starting compound to the alkoxide of the subject element and precipitation of the ammonium halide or the alkali or alkaline earth metal halide. In a second step, the alkoxide is hydrolyzed with water, producing the oxide (or hydroxide or hydrated oxide) of the subject element. Oxides and hydroxides produced in accordance with the invention have non-detectable levels of halide-containing species, e.g., below about 5 ppm and even below 1 ppm.

DETAILED DESCRIPTION OF THE PREFERRED EMBODIMENTS

Oxides of subject elements, particularly transition metals (M), including rare earths, are produced from the corresponding halides (MX) by alcoholysis followed by hydrolysis according to the general two-step reaction sequence:

$$MX_n + nHOR \rightarrow M(OR)_n + nHX \qquad \text{I.}$$

$$M(OR)_n + (n/2)H_2O \rightarrow MO_{n/2} + nHOR \qquad \text{II.}$$

Although each of reaction steps I and II are separately well known, it was heretofore unappreciated that the two-step procedure would yield oxides of certain subject elements that are of much higher purity than previously achieved, particularly with respect to reduced halide content. Oxides of a number of metals, which are not practically producible by direct oxidation of the elemental metals, are often produced by direct hydrolysis of the corresponding halide, and metal oxides of sufficient purity for most applications are obtained. Recent technology, such as laser optics, required oxides of extremely high purity metal, but it has been found that metal oxides produced by metal halide hydrolysis may contain unacceptable levels of halides for particular applications. The halides are present as moieties of mixed metal oxide/halides which are not readily separable from the metal oxides.

The process of the present invention is generally applicable to producing oxides and hydroxides of subject elements from the corresponding halides of the subject elements, providing certain criteria are met. The subject element halide must react with an alcohol plus a replacement species, such as ammonia or an alkali or alkaline earth metal, to form an alkoxide of the subject element. The subject element alkoxide must be soluble in the alcohol, or at least substantially more soluble than halide salts.

Of particular interest herein is the formation of transition metal oxides and rare earth metal oxides from the corresponding transition metal halides and rare earth metal halides. That is, the invention is primarily concerned with the metals of groups IB–VIIIB of the periodic table and the lanthanide and actinide series. Oxides and hydroxides of certain metals and metalloids of groups IIIA–VIA may also be formed in this manner, particularly germanium and arsenic. Because the invention is primarily concerned with the formation of pure metal oxides, much of the discussion herein describes the subject element as being a metal; but it is to be understood the invention applies to certain metalloids such as germanium and arsenic. Generally, the invention does not apply to producing alkali metal oxides because it is either inapplicable or is of little value relative to other alternatives. The method may be used to produce oxides or hydroxides of certain alkaline earth metals, but more practical methods of producing pure oxides or hydroxides of alkaline earth metals are generally available. The invention also does not apply to forming oxides of elements, such as iron, which do not form alkoxides by reaction I.

Throughout the description of the invention, the product is often referred to as a "metal oxide," and indeed that is the species which is produced with several subject elements, particularly elements of group VB of the periodic table which includes niobium and tantalum. In cases of other subject elements, the species which is actually produced is the hydroxide or a hydrated form of the oxide, and the invention herein is intended to cover synthesis of pure forms of these species as well. Herein, the term "oxides" is intended to cover hydrated forms of the same. If a hydrated oxide or a hydroxide is the species which is produced upon hydrolysis, it is generally true that the corresponding oxide can be produced by heating to drive off the water. If the end use application of the purified product requires exposure to aqueous medium, e.g., in crystal growing, it is generally considered to be immaterial whether the species is the oxide, hydroxide or hydrated oxide, providing a high purity is achieved, i.e., very low or non-detectable halogen content.

The two-step reaction procedure of metal oxide or hydroxide preparation according to this invention cannot compete in efficiency with direct hydrolysis of metal halides in the general production of metal oxides and hydroxides and would not ordinarily be even considered as a practical procedure for producing metal oxides; however, because it is found that the two-step procedure can be controlled to yield metal oxides which are completely free of halides, the two-step procedure is considered highly valuable for producing metal oxides and hydroxides where rigid standards of purity are required. By "completely free of halides" is meant halide levels below detectable levels, particularly below about 10 ppm.

In addition to substantially removing all traces of halide, the two-step process of the present invention results in a purification of the product oxide or hydroxide relative to the starting halide, removing elements, such as iron, which do not form alkoxides. Thus for example, whereas available $TaCl_5$ generally contains minor amounts of iron, $Ta_2O_5$ prepared in accordance with the present invention is substantially free of iron. Metal impurities, like halide impurities, can be detrimental to certain end use applications of the subject element oxide, or hydroxide and removal of elements that do not form alkoxides represents an important advantage of the method of the present invention.

An important aspect of the procedure of the present invention is that the alcoholysis of the subject element halide is facilitated by a species such as ammonia, an alkali metal or an alkaline earth metal which reacts with the halide, forming the corresponding halide salt. Another important aspect of the procedure of the present invention is that the alcoholysis of the metal halide is conducted in a water-free alcohol in which the metal alkoxide is soluble but in which halide salts are insoluble, resulting in immediate precipitation of the product salt halide and removal of the halide from the alkoxide-in-alcohol solution. Physical separation of the solution from the precipitate results in a metal alkoxide-in-alcohol solution which is substantially completely free of halide.

A large stoichiometric excess of alcohol is used relative to the metal halide. As the reaction is typically carried out in alcohol with the metal halide suspended, e.g., particles suspended by stirring, a large excess of alcohol is present. The excess of alcohol helps to ensure complete removal of the halide from the metal. Gradually, the stoichiometric excess of alcohol is at least tenfold, but may be much greater. A sufficient volume of the alcohol is provided to dissolve all of the alkoxide which forms, the amount required depending upon the solubility of the alkoxide in the alcohol.

The alcohol is water-free and may be exposed to a desiccant prior to use to ensure dryness. Any desiccant should be halide-free. The alcohol is generally used neat, but may be used in conjunction with a suitable organic solvent in which the product halide salt is insoluble.

It may be appreciated that the use of an organic solvent and the excess quantities of both the alcohol and halide-reactive species represent production costs which are ordinarily prohibitive relative to direct hydrolysis of chlorides. However, these costs are easily justified where high purity metal oxides are required for specific highly technical purposes, such as growing crystals for lasers. Thus, although the specific reactions of this procedure were previously known, the protocol described herein was not previously considered as suitable for the production of metal oxides.

A convenient halide-reactive replacement species is ammonia, which can be bubbled through the solvent in amounts and for a period of time sufficient to ensure complete removal of the halide as ammonium halide ($NH_4X$). Alternatively, metal may be used as the halide-reactive species, particularly alkali metals, such as sodium, potassium or lithium, or even some of the more reactive alkaline earth metals, such as magnesium or calcium. If a reactive metal is used as the replacement species, it is generally prereacted with the alcohol to form the reactive metal alkoxide.

The starting compound, e.g., a metal halide, is provided in as pure a state as is available. Halides of sufficient purity are obtainable, for example, from Alfa Products, Danvers, Mass. Generally, the metal halides are bromides or chlorides, and less frequently iodides. Because solvents are used in which metal halides are substantially insoluble, the transition metal halides are provided in particulate form and are suspended, e.g., by continuous stirring, in the water-free organic solvent. To facilitate their suspension in alcohol and to increase contact with the reacting species, the metal halide is preferably finely divided, e.g., 60 standard mesh or finer. Alcoholysis is continued until the suspended particles are fully converted to the corresponding metal alkoxides; however, any unreacted metal halide is physically separable from the solution and does not contaminate the final product.

The alcohol, which is used both as the liquid phase and as a reactant, is not considered to be particularly important so long as the metal alkoxide which is produced is soluble therein. Suitable alcohols include short chain (8 or less carbon atoms) saturated or unsaturated, branched or unbranched alcohols. Phenol and phenol derivatives are also suitable. Generally, either methanol or ethanol is the alcohol of choice, being inexpensive and relatively reactive with metal chlorides. Ethanol and methanol have the additional advantage of boiling at low temperature, facilitating their evaporation from the alkoxides which form.

Subsequent to completion of the alcoholysis, the metal alkoxide-in-alcohol solution is physically separated from the insoluble halide salt and any unreacted precursors. To ensure removal of very fine precipitate particles, decantation of the solution may be followed by centrifugation or even microfiltration.

The alcohol is generally removed by evaporation before the hydrolysis step. However, the metal alkoxide-containing solution could be directly contacted with water.

Water used in the hydrolysis must meet strict standards of purity, and in particular must be free of halides and of metal ions. Preferably, 18 mega ohm water is used for hydrolysis.

In the presence of water, hydrolysis of the metal alkoxide proceeds rapidly and hydrolysis conditions, such as temperature, are not considered to be particularly critical. The metal oxide or hydroxide that is produced may or may not be soluble in water, and if insoluble will form as a precipitate, facilitating removal from the water. In any case, the water is removable by subsequent evaporation.

Of particular interest herein is the production of niobium oxide and tantalum oxide, each elements of group VB of the periodic chart. As discussed above, these oxides are used in the process of growing crystals of LiNbO$_3$ and LiTaO$_3$, a process to which the presence of halides is highly detrimental. Specific reactions by which halide-free Nb$_2$O$_5$ and Ta$_2$O$_5$ are produced from chlorides proceed as follows:

A   2 TaCl$_5$ + 10 EtOH + 10 NH$_3$ → 2 Ta(OEt)$_5$ + 10 NH$_4$Cl

B   2 Ta(OEt)$_5$ + 5 H$_2$O → Ta$_2$O$_5$ + 10 EtOH

A$^1$  2 NbCl$_5$ + 10 EtOH + 10 NH$_3$ → 2 Nb(OEt)$_5$ + 10 NH$_4$Cl

B$^1$  2 Nb(OEt)$_5$ + 5 H$_2$O → Nb$_2$O$_5$ + 10 EtOH

The alkoxides of both Ta (V) and Nb (V) are liquids at room temperature and are readily soluble in the corresponding alcohols.

The invention will now be described in greater detail by way of specific examples.

EXAMPLE 1

45.3 g of TaCl$_5$ was placed in a 2 liter flask with stirring bar. Under a nitrogen atmosphere 1 liter ethanol was added slowly to allow HCl evloution. Ammonia was bubbled through the solution for 72 hours. The filtrate was recovered and washed with benzene. 31.2 g of Ta(OEt)$_5$ was recovered.

2Ta(OC$_2$H$_5$)$_5$ + 5H$_2$O → Ta$_2$O$_5$ + C$_2$H$_5$OH 17.1 g. of Ta(OEt)$_5$ (42.1 mmol) was slowly added to a microware flask containing 10 g. H$_2$O, by dropping funnel, with magnetic stirring. (The Ta(OEt)$_5$ was placed in the dropping funnel in a purged glove bag.) The material formed a cake and also gave off an exotherm. The cake was easily broken up with a small spatula, forming a grainy white solid. The batch was filtered on a fritted disk filter in a Buchner funnel. The filtration went very slowly and was speeded up slightly by stirring the material in the funnel. When the cake went dry it was washed with about 10 ml. H$_2$O. When it went dry again the funnel was placed in a drying oven at 115° C. and 29 inches (Hg) vacuum (3.4 × 10$^3$ N/m$^2$ pressure), and left to dry over the weekend.

The material later slightly discolored to tan. Total material isolated was 9.5 g., indicating quantitative reaction.

Analysis showed less than 10 ppm chloride. Elemental analysis showed 85.3% tantalum. (The theoretical proportion of tantalum is 81.9%.)

EXAMPLE 2

30.5 g of NbCl$_5$ was placed in a 2 liter flask with stirring bar. Under a nitrogen atmosphere 1 liter ethanol was added slowly to allow HCl evloution. Ammonia was bubbled through the solution for 72 hours. The filtrate was recovered and washed with benzene. 24.8 g of Nb(OEt)$_5$ was recovered.

2Nb(OC$_2$H$_5$)$_5$ + 5H$_2$O → Nb$_2$O$_5$ + C$_2$H$_5$OH 14.0 g. of Nb(OEt)$_5$ (44.0 mmol) was slowly added to a microware flask containing 10 g. H$_2$O, by dropping funnel, with magnetic stirring. (The Nb(OEt)$_5$ was placed in the dropping funnel in a purged glove bag.) The material formed a cake and also gave off an exotherm. The cake was easily broken up with a small spatula, forming a grainy white solid. The batch was filtered on a fritted disk filter in a Buchner funnel. The filtration went very slowly and was speeded up slightly by stirring the material in the funnel. When the cake went dry it was washed with about 10 ml. H$_2$O. When it went dry again the funnel was placed in a drying oven at 115° C. and 29 inches (Hg) vacuum (3.4 × 10$^3$ N/m$^2$ pressure), and left to dry over the weekend.

The material later slightly discolored to tan. Total material isolated was 5.8 g., indicating quantitative reaction.

While the invention has been described in terms of certain preferred embodiments, modifications obvious to one with ordinary skill in the art may be made without departing from the scope of the invention. For example, metal oxides and hydroxides produced by conventional methods and containing significant amounts of chloride may be converted to highly purified metal oxides by the two-step reaction procedure. The metal oxide that contains mixed oxide/halide contaminating species and even very low concentrations of metal halides might be exposed to an alcohol and a replacement species, whereupon the alkoxide group replaces the halide contaminants. Subsequent hydrolysis produces purified metal oxide. For the purpose of this invention, such a procedure is considered to be the equivalent of starting with the metal halide.

Various features of the invention are set forth in the following claims.

What is claimed is:

1. A method for producing a halide-free oxide or hydroxide of a subject element from the corresponding subject element halide, comprising:
   in a first reaction step, providing a liquid medium comprising a water-free alcohol and contacting said alcoholic medium with the subject element halide and further contacting said alcohol and said subject element halide with a replacement species that reacts with halides, said alcohol being provided at at least about a ten-fold stoichiometric excess relative to said subject element halide, thereby producing a subject element alkoxide and a salt of the replacement species and the halide, said alcohol being selected such that the subject element alkoxide is soluble in said medium and said replacement halide salt is insoluble and precipitates from said medium,
   physically separating said medium containing said alkoxide from said precipitate salt, and
   in a second reaction step, hydrolyzing said subject element alkoxide with 18 mega ohm purity water to produce the corresponding subject element oxide or subject element hydroxide.

2. A method according to claim 1 wherein said replacement species is selected from the group consisting of ammonia, alkali metals and alkaline earth metals.

3. A method according to claim 1 wherein the said subject element is a member of groups IB–VIIIB, a member of groups IIIA–VIA or a member of the lanthanide and actinide series of the periodic table.

4. A method according to claim 1 wherein the subject element is selected from the metals of Group VB of the periodic table.

5. A method according to claim 1 wherein the subject element is tantalum or niobium.

6. A method according to claim 1 wherein said halide moiety of the subject element halide is selected from the group consisting of chlorine, bromine and iodine.

7. A method according to claim 1 wherein the subject element halide is a pentavalent halide of tantalum or niobium.

8. A method according to claim 1 wherein said replacement species is ammonia and said ammonia is continuously bubbled through said alcohol.

9. A method according to claim 1 wherein said subject element halide is insoluble in said selected alcohol, said subject element halide being in the form of particulates, said particulates being suspended in said selected alcohol.

10. A method according to claim 1 wherein said subject element halide is in the form of particulates of 60 Standard mesh or finer.

11. A method for producing a halide-free oxide or hydroxide of a subject element from the corresponding subject element halide, comprising:

in a first reaction step, providing a medium comprising water-free alcohol and contacting said alcoholic medium with the subject element halide, said alcohol being provided at at least about a ten-fold stoichiometric excess relative to said subject element halide, contacting said alcohol and said subject element halide with an excess of ammonia, thereby producing a subject element alkoxide and an ammonium halide salt, said alcohol being selected such that the subject element alkoxide is soluble in said medium and said ammonium halide salt is insoluble and precipitates said medium, physically separating said alkoxide-containing medium from said precipitated salt, and in a second reaction step, hydrolyzing said subject element alkoxide with 18 mega ohm purity water to produce the corresponding subject element oxide or subject element hydroxide.

12. A method for producing a halide-free oxide or hydroxide of a subject element from the corresponding subject element halide, comprising:

in a first reaction step, providing a medium consisting essentially of a water-free alcohol and contacting said alcoholic medium with the subject element halide and further contacting said alcoholic medium and said subject element halide with an excess of ammonia, producing a subject element alkoxide and an ammonium halide salt, said alcohol being selected such that the subject element alkoxide is soluble therein and said ammonium salt is insoluble and precipitates therefrom, physically separating said alkoxide-in-alcohol solution from said precipitated salt, and in a second reaction step, hydrolyzing said subject element alkoxide with 18 mega ohm purity water to produce the corresponding subject element oxide or subject element hydroxide.

* * * * *